(12) United States Patent
Hayashi et al.

(10) Patent No.: US 7,560,091 B2
(45) Date of Patent: Jul. 14, 2009

(54) WATER REFORMING METHOD AND WATER REFORMER

(75) Inventors: Hidemitu Hayashi, Tokyo (JP); Kiyoshi Kimura, Abiko (JP)

(73) Assignee: Hidemitu Hayashi, Tokyo (JP)

( * ) Notice: Subject to any disclaimer, the term of this patent is extended or adjusted under 35 U.S.C. 154(b) by 655 days.

(21) Appl. No.: 11/389,069

(22) Filed: Mar. 27, 2006

(65) Prior Publication Data
US 2007/0128104 A1 Jun. 7, 2007

(30) Foreign Application Priority Data
Dec. 5, 2005 (JP) .............................. 2005-350381

(51) Int. Cl.
*C02F 1/70* (2006.01)
(52) U.S. Cl. .................... 423/657; 423/652; 423/658.2
(58) Field of Classification Search .................. 423/657
See application file for complete search history.

(56) References Cited

U.S. PATENT DOCUMENTS 6,834,623 B2 * 12/2004 Cheng ......................... 123/1 A 2005/0121399 A1 * 6/2005 Hayashi et al. ............. 210/749

FOREIGN PATENT DOCUMENTS

| JP | 2611080 B2 | 5/1997 |
|----|------------|--------|
| JP | 2615308 B2 | 5/1997 |
| JP | 2623204 B2 | 6/1997 |
| JP | 2002-336877 A | 11/2002 |
| JP | 2004-41949 A | 2/2004 |
| JP | 2004-243151 A | 9/2004 |
| JP | 2005-161209 A | 6/2005 |

* cited by examiner

*Primary Examiner*—Melvin C Mayes
*Assistant Examiner*—Kenneth Vaden
(74) *Attorney, Agent, or Firm*—Birch, Stewart, Kolasch & Birch, LLP

(57) ABSTRACT

Mineral particles consisting essentially of metallic magnesium particles subjected to special processing are accommodated directly in a microporous cartridge made of a sintered polypropylene material, and the cartridge is closed. The cartridge is put in a closed raw water container, whereby a large amount of hydrogen gas is generated in a short period of time and released from the whole surface of the cartridge in the form of microbubbles so as to be dissolved in raw water in the container.

10 Claims, 4 Drawing Sheets

WATER REFORMING METHOD AND WATER REFORMER

BACKGROUND OF THE INVENTION

1. Field of the Invention

The present invention relates to a water reforming method and a water reformer.

2. Discussion of Related Art

Water is a compound of hydrogen (H) and oxygen (O) combined in the ratio of 2:1. The covalent bonding energy that binds hydrogen with oxygen is so strong that the hydrogen and oxygen will not readily separate from each other. Accordingly, hydrogen cannot normally exist alone in water. Hydrogen is the lightest gas in space. Therefore, even if it is dissolved in water, hydrogen readily escapes into the atmosphere. From this fact, it can be said that almost all water found on the earth is hydrogen-poor water (from which hydrogen has disappeared).

The most recent biomedical research has revealed that active oxygen is implicated in various diseases and aging. It is therefore necessary to take measures to suppress or eliminate disorder (oxidative damage) caused by active oxygen. It goes without saying that the best countermeasure against oxidative damage is reduction process from the theoretical point of view. The term "reduction process" can be said to have been originally given to the action of hydrogen atoms. This will be clear from the statement in junior high school science textbooks that "oxidation is combining with oxygen, and reduction is combining with hydrogen or removal of oxygen".

It may be surmised from the above-described hydrogen-poor water (water from which hydrogen has disappeared) that the greatest reason why mankind has been suffering from various diseases is that we have been drinking hydrogen-poor water, that is, water incompetent to suppress or eliminate oxidative damage by active oxygen. In other words, hydrogen-poor water may be said to be "disease-causing water".

Meanwhile, water containing an abundance of hydrogen (hydrogen-rich water) is expected to be necessary as more effective water for preventing and curing diseases. Hydrogen is found in two forms: atomic hydrogen and molecular hydrogen. Atomic hydrogen has a very short lifetime (its half-life is considered to be about $1/3$ second). Accordingly, drinking of water containing an abundance of atomic hydrogen is practically impossible. The lifetime of molecular hydrogen, which consists of two hydrogen atoms, is considered to be about 1,000 seconds (10-odd minutes). Therefore, a practically effective way is to drink water in which an abundance of molecular hydrogen is dissolved.

It is surmised that molecular hydrogen taken up by our body is split into atomic hydrogen having very strong reducing power (hence also known as "active hydrogen") by hydrogenases (i.e. enzymes that split molecular hydrogen into atomic hydrogen) in the body, and that the active hydrogen suppresses and eliminates, by its reducing action, oxidative damage by active oxygen in the body.

Natural water that is said to contain an abundance of hydrogen is found at various places in the world. Examples of such natural water are "Lourdes water" (France), "Tlacote water" (Mexico), and "Nordenau water" (Germany). These are attracting worldwide attention as miraculous healing water that can cure all kinds of diseases. It is said that anyone can cure diseases simply by drinking the healing water.

Under these circumstances, the present inventor (Hayashi) has conducted exhaustive research for many years to artificially produce miraculous healing water capable of curing, all kinds of diseases, and has already filed the following four applications for patent as inventions having the same object.

(1) Japanese Patent Application Unexamined Publication (KOKAI) No. 2002-336877:

"An active hydrogen water producing apparatus having a container that is provided with windows for water to come in and out of the container and that has magnesium metal sealed therein."

(2) Japanese Patent Application Unexamined Publication (KOKAI) No. 2004-41949:

"A hydrogen-rich water generating method wherein drinking water and magnesium particles are allowed to react with each other to generate hydrogen gas, thereby changing the drinking water into hydrogen-rich water containing an abundance of hydrogen."

"A hydrogen-rich water generating method wherein drinking water is allowed to react with silver particles, together with magnesium particles, so that hydrogen-rich water is purified by the silver particles."

"A hydrogen-rich water generator having a casing that can be immersed in a drinking water bottle and that allows the drinking water to enter it, and a water-permeable bag put in the casing and filled with magnesium particles that react with the drinking water to generate hydrogen gas."

(3) Japanese Patent Application Unexamined Publication (KOKAI) No. 2004-243151:

"A hydrogen-dissolved water producing device including a hydrogen-generating material (metallic magnesium) that generates hydrogen gas through a catalytic reaction with drinking water, and a cover member having in its interior space an accommodating section capable of accommodating the hydrogen-generating material, wherein the covering member is formed to allow the drinking water to flow in and out of it, and the hydrogen-generating material is accommodated in the accommodating section."

(4) Japanese Patent Application Unexamined Publication (KOKAI) No. 2005-161209:

"A hydrogen-rich water generating method and generator wherein drinking water and magnesium particles accommodated in a water-permeable ceramic casing are allowed to react with each other in a container to generate hydrogen gas, thereby changing the drinking water into hydrogen-rich water containing an abundance of hydrogen."

In the above-described inventions, magnesium particles are accommodated in a cartridge made of a synthetic resin and provided with a plurality of water passing holes, and the casing is immersed in raw water in a drinking water container, thereby generating hydrogen gas to produce hydrogen-rich water. It is intended to erase active oxygen from our body by drinking the hydrogen-rich water, thereby eliminating causes of various diseases. The amount of hydrogen gas generated per unit time, however, is very small, which is a problem to be solved.

The above-described Japanese Patent Application Unexamined Publication (KOKAI) No. 2005-161209 mentions using as a cartridge a ceramic casing that allows water to penetrate therethrough into the interior thereof. In this regard, the following has been pointed out. If the ceramic cartridge is an unglazed product, water can penetrate therethrough, and hydrogen gas can be generated in the cartridge, but much time is needed for the hydrogen gas to flow out of the cartridge and to dissolve in the raw water in the container. In addition, the ceramic cartridge is heavy in weight and easily breakable upon falling. Thus, the invention disclosed in the above-described publication lacks practical applicability and has not yet been carried out.

It should be noted that the present inventor (Hayashi) got the idea of hydrogen-rich water originally from studies about electrolyzed water (reduced water), and the present invention makes it no longer necessary to use an electrolyzer, which has been conventionally required to produce hydrogen-rich water.

Examples of electrolyzed water producing method include Japanese Patent Nos. 2611080, 2615308 and 2623204. The present inventor (Hayashi) has found, however, that hydrogen water produced by these electrolytic processes is defective. That is, because hydrogen is the lightest substance in space, even if dissolved in water, hydrogen gas all escapes from the water within only several minutes, resulting in hydrogen water returning to ordinary tap water (hydrogen-poor water).

Consequently, it has become necessary for the present inventor (Hayashi), who has published many books and theses on electrolyzed water, to change his point of view entirely.

SUMMARY OF THE INVENTION

Accordingly, an object of the present invention is to improve the above-described conventional cartridge to prepare a cartridge capable of increasing the amount of hydrogen gas generated per unit time, thereby providing a novel method and device for reforming water such as drinking water.

The present invention provides a water reforming method wherein metallic magnesium particles subjected to special processing are accommodated directly in a microporous cartridge made of a sintered polypropylene material, and the cartridge is closed. The cartridge thus prepared is put in a closed raw water container, whereby a large amount of hydrogen gas is generated and released from the whole surface of the cartridge in the form of microbubbles so as to be dissolved in raw water in the container.

In addition, the present invention provides a water reformer including a microporous cartridge made of a sintered polypropylene material. Metallic magnesium particles subjected to special processing are accommodated directly in the cartridge, and the cartridge is closed. The cartridge thus prepared is put in a closed raw water container, whereby a large amount of hydrogen gas is generated and released from the whole surface of the cartridge in the form of microbubbles so as to be dissolved in raw water in the container.

According to the present invention, the cartridge for accommodating the metallic magnesium particles is a microporous member made of a sintered polypropylene material. Therefore, a large amount of hydrogen gas generated from the magnesium particles in the cartridge is released from the whole surface of the cartridge into the raw water in the container in the form of microbubbles with a diameter of about 1 mm, thereby making it possible to produce drinking water filled with hydrogen gas.

Black silica may be accommodated in the cartridge, together with the metallic magnesium particles. Black silica emits strong growth rays of far-infrared radiation at ordinary temperature. Therefore, addition of black silica contributes to exhibiting a curative effect.

Addition of titanium balls enables antibacterial and antiviral activities to be induced to exhibit a water purification effect.

Because the cartridge is made of a sintered polypropylene material, the hydrogen water generation efficiency can be increased effectively.

In an experiment we conducted, the cartridge accommodating the above-described particles was immersed in raw water in a 500 ml PET bottle for about 12 hours. As a result, a large amount of microbubbles was released from the cartridge, and the bottom recess of the PET bottle was expanded by the hydrogen partial pressure and deformed into a substantially planar shape.

Such a phenomenon was not observed in the conventional synthetic resin cartridge. Therefore, it is clear that the direct cause of the deformation of the bottle's bottom recess is that hydrogen gas generated from the metallic magnesium in the microporous cartridge was released through the cartridge surface in large quantity in the form of microbubbles.

The microbubbles are normally observed adhering to the cartridge surface. If the bottle is shaken, the microbubbles are released into water in large quantity.

In the present invention, the raw water in the container reacts with the magnesium particles to generate hydrogen gas according to the following chemical formula:

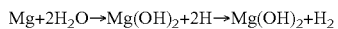

$$Mg+2H_2O \rightarrow Mg(OH)_2+2H \rightarrow Mg(OH)_2+H_2$$

Mg=metallic magnesium, $2H_2O$=water,
$Mg(OH)_2$=magnesium hydroxide,
2H=atomic hydrogen (active hydrogen),
$H_2$=molecular hydrogen (hydrogen gas)

As a result, the raw water at ordinary temperature or cooled in the container changes into water containing an abundance of hydrogen. The hydrogen gas content in the water can be measured with a hydrogen sensor.

It is the conventionally accepted view in the world of chemistry that metallic magnesium does not react with water at ordinary temperature, but only when finely-divided metallic magnesium powder is heated in water, it reacts with the water to form magnesium hydroxide and hydrogen gas. It was, however, confirmed by examination of the reaction of magnesium particles in the above-described example with a hydrogen sensor that magnesium readily reacts with water, whether at ordinary temperature (25° C.) or cooled (5° C.), to form magnesium hydroxide and hydrogen gas.

These and other features and advantages of the present invention will be described in more detail below with reference to the associated figures.

BRIEF DESCRIPTION OF THE DRAWINGS

The following detailed description can be more fully understood when considered in conjunction with the drawings in which.

DETAILED DESCRIPTION OF THE INVENTION

The water reforming method and water reformer according to the present invention will be explained below with reference to the accompanying drawings.

In FIGS. 1 to 4, a microporous cartridge 1 used in the present invention is made of a sintered polypropylene material in its entirety. The shape and size of the cartridge 1 may be varied according to each particular application. The cartridge 1 has various unevennesses and micropores in the surface thereof. The size of the micropores is from 100 to 200 microns. In the following experiment, a microporous cartridge having a mean pore size of 150 microns was used, and it was experimentally proved to be able to generate a maximum amount of hydrogen gas.

If the sintered polypropylene cartridge 1 is formed with micropores having a pore size not smaller than 200 microns, powder generated by friction between mineral particles (described later) is likely to flow out through the cartridge surface, causing water in the container to be contaminated.

A stopper 2 for closing the opening of the cartridge 1 is made of the same material as the cartridge 1.

Figure 1:
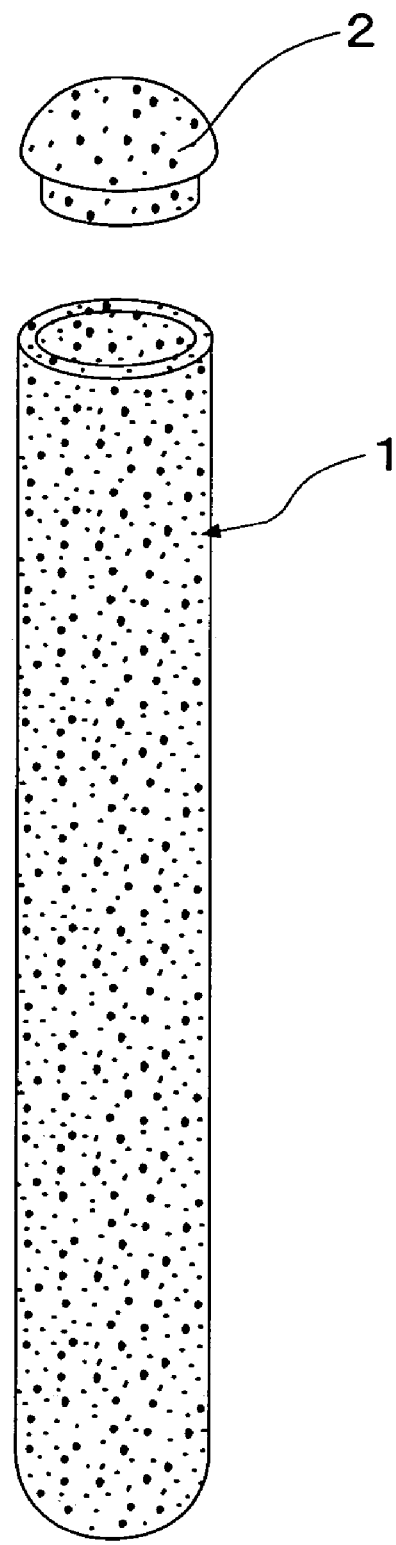
FIG. 1 is a perspective view of a cartridge used in the present invention.
Figure 2:
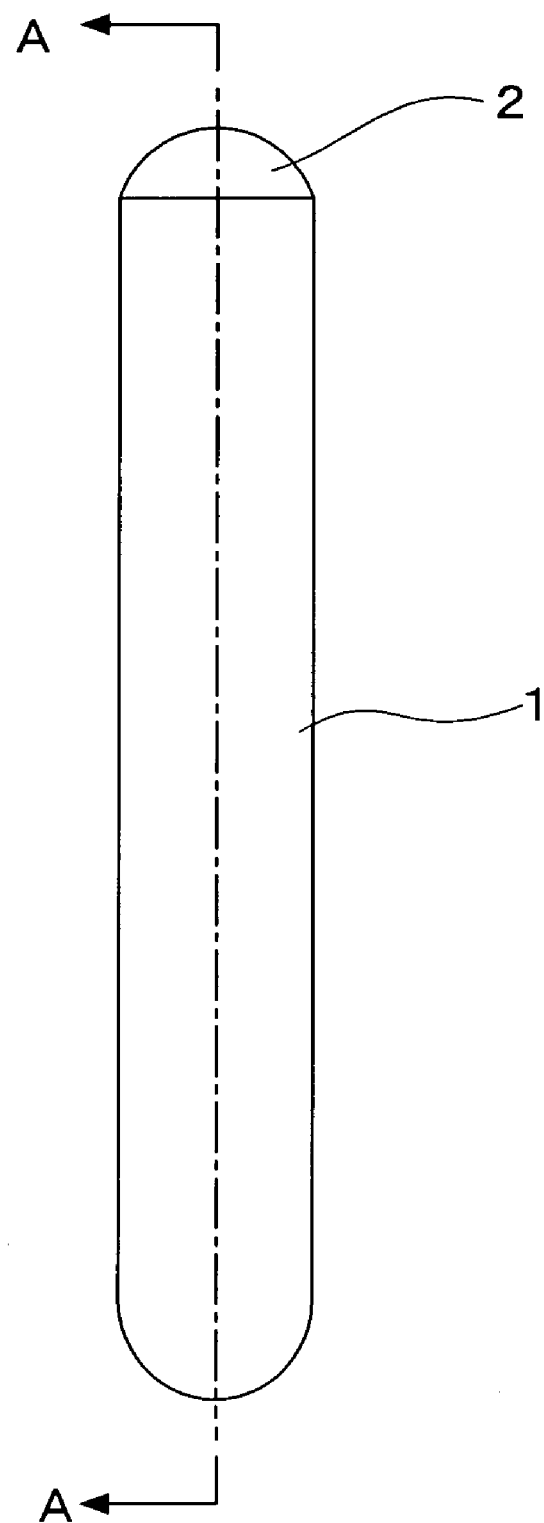
FIG. 2 is a front view of the cartridge.
Figure 3:
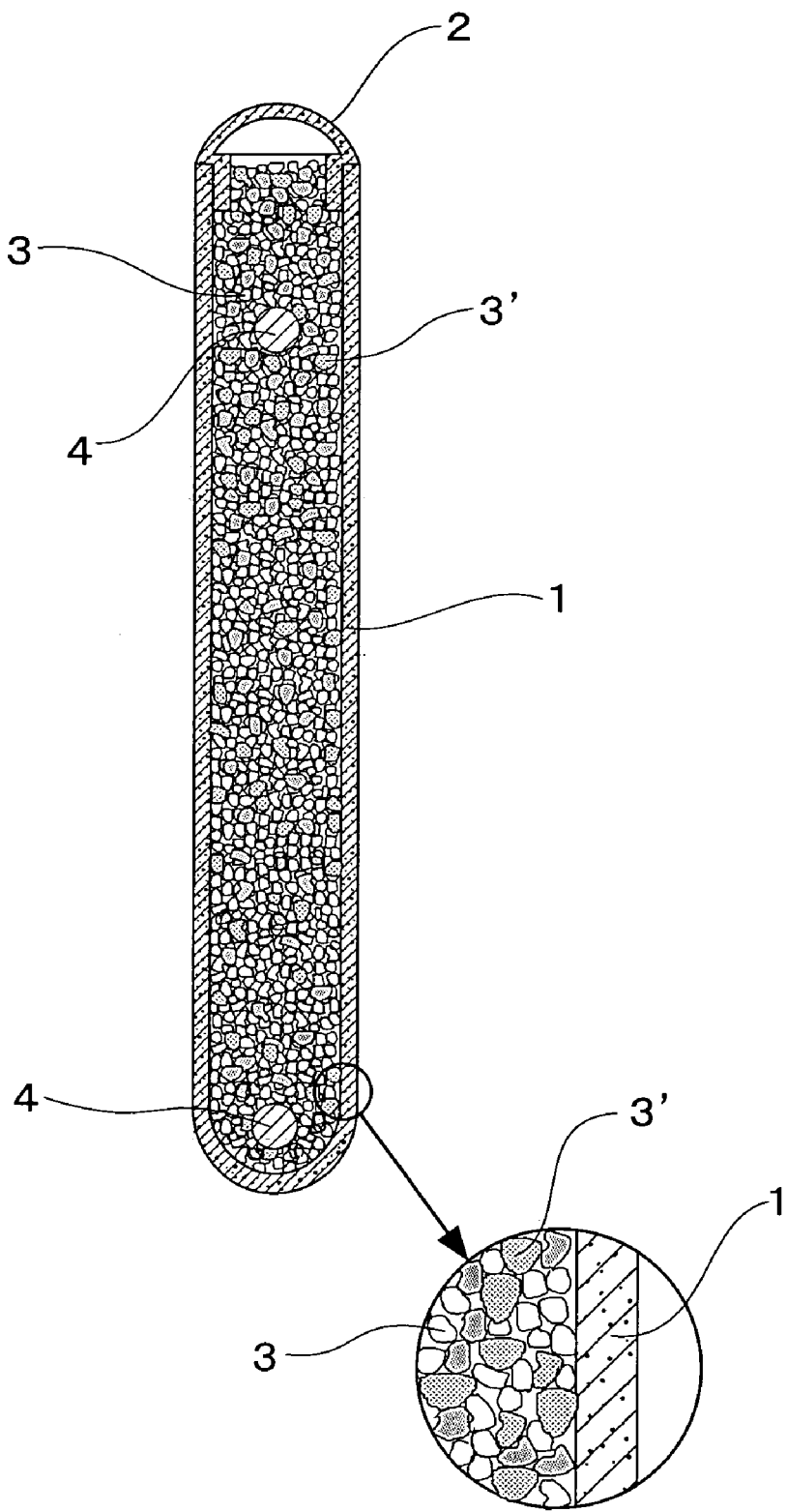
FIG. 3 is a sectional view taken along the line A-A in FIG. 2.

As shown in FIG. 3, metallic magnesium particles 3 are accommodated directly in the cartridge 1.

The metallic magnesium particles 3 are subjected to special processing to promote generation of a large amount of hydrogen gas.

The special processing applied to the metallic magnesium particles 3 is firing carried out at a temperature of 115° C. plus or minus 5° C. for a time period of 15 minutes plus or minus 5 minutes.

Other mineral particles, e.g. black silica 4 and titanium balls 5, may be added to the metallic magnesium particles 3. Black silica emits strong far-infrared radiation at ordinary temperature. Among far-infrared rays, those in the wavelength range of about 4 to 14 microns, in particular, are called "growth rays". Black silica mainly emits the growth rays and is therefore expected to bring about a healing effect and an animal and plant activating effect.

If a plurality of titanium balls 5 having a photocatalytic action are used, it is possible not only to decompose malodorous substances but also to induce antibacterial and antiviral activities to exhibit a water purification effect. Titanium balls have been proved to be capable of sterilizing *Legionella* species. The titanium balls 5 are formed by a technique wherein ceramic balls are subjected to high-speed blasting with metallic titanium powder to effect surface treatment and to form titania coating ($TiO_2$).

Figure 4:
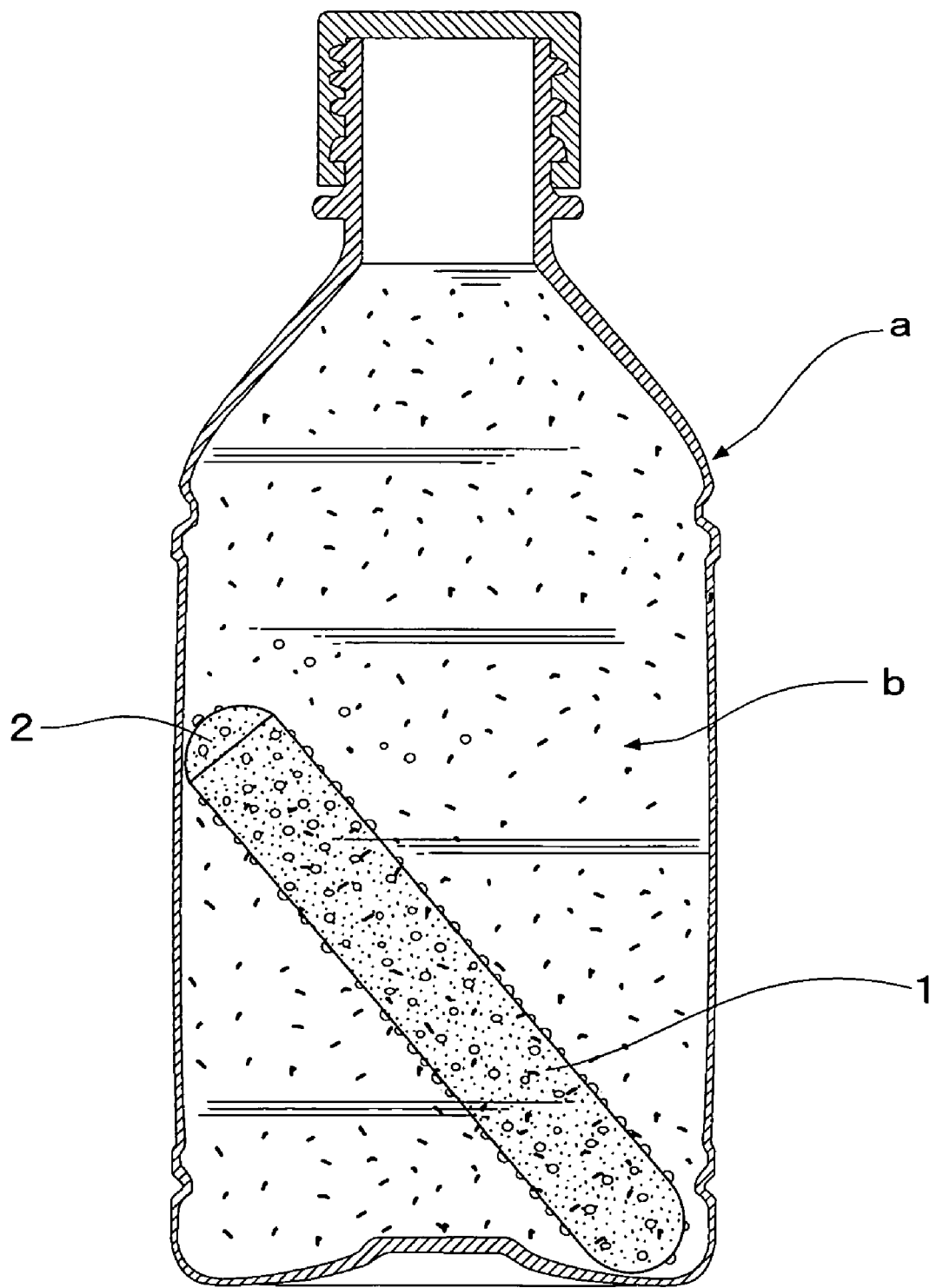
FIG. 4 is a vertical sectional view showing the way in which action takes place in a water container.

FIG. 4 shows the way in which the microporous cartridge 1 is actually used in a container a containing drinking water b.

It should be noted that the application of the water reforming method and water reformer according to the present invention is not necessarily limited to treatment of drinking water. The present invention is also applicable to treatment of water used for eye, face or body washing and other purposes. In addition, the present invention is not limited to the foregoing embodiments but can be modified in a variety of ways.

What is claimed is:

1. A water reforming method comprising the steps of:
    preparing a microporous cartridge made of a sintered polypropylene material, said cartridge directly accommodating metallic magnesium particles that have been subjected to special processing comprising firing carried out at a temperature of 115° C. plus or minus 5° C. for a time period of 15 minutes plus or minus 5 minutes and being closed; and
    putting said cartridge in a closed raw water container, whereby a large amount of hydrogen gas is generated in a short period of time and released from a whole surface of said cartridge in a form of microbubbles so as to be dissolved in raw water in the container.

2. A water reformer comprising: a microporous cartridge made of a sintered polypropylene material; and
    metallic magnesium particles subjected to special processing that are accommodated directly in said cartridge, said cartridge being closed after said metallic magnesium particles that have been subjected to special processing comprising firing carried out at a temperature of 115° C. plus or minus 5° C. for a time period of 15 minutes plus or minus 5 minutes; wherein said cartridge is put in a closed raw water container, whereby a large amount of hydrogen gas is generated in a short period of time and released from a whole surface of said cartridge in a form of microbubbles so as to be dissolved in raw water in the container.

3. A water reforming method comprising the steps of:
    preparing a microporous cartridge made of a sintered polypropylene material, said cartridge directly accommodating metallic magnesium particles that have been subjected to special processing comprising firing carried out at a temperature of 115° C. plus or minus 5° C. for a time period of 15 minutes plus or minus 5 minutes and being closed and black silica and being closed; and
    putting said cartridge in a closed raw water container, whereby a large amount of hydrogen gas is generated in a short period of time and released from a whole surface of said cartridge in a form of microbubbles so as to be dissolved in raw water in the container.

4. A water reformer comprising:
    a microporous cartridge made of a sintered polypropylene material; and
    metallic magnesium particles that have been subjected to special processing comprising firing carried out at a temperature of 115° C. plus or minus 5° C. for a time period of 15 minutes plus or minus 5 minutes and black silica that are accommodated directly in said cartridge, said cartridge being closed after said metallic magnesium particles and black silica have been accommodated therein;
    wherein said cartridge is put in a closed raw water container, whereby a large amount of hydrogen gas is generated in a short period of time and released from a whole surface of said cartridge in a form of microbubbles so as to be dissolved in raw water in the container.

5. A water reforming method comprising the steps of:
    preparing a microporous cartridge made of a sintered polypropylene material, said cartridge directly accommodating metallic magnesium particles that have been subjected to special processing comprising firing carried out at a temperature of 115° C. plus or minus 5° C. for a time period of 15 minutes plus or minus 5 minutes and titanium balls and being closed; and
    putting said cartridge in a closed raw water container, whereby a large amount of hydrogen gas is generated in a short period of time and released from a whole surface of said cartridge in a form of microbubbles so as to be dissolved in raw water in the container.

6. A water reformer comprising:
    a microporous cartridge made of a sintered polypropylene material; and
    metallic magnesium particles that have been subjected to special processing comprising firing carried out at a temperature of 115° C. plus or minus 5° C. for a time period of 15 minutes plus or minus 5 minutes and titanium balls that are accommodated directly in said cartridge, said cartridge being closed after said metallic magnesium particles and titanium balls have been accommodated therein;
    wherein said cartridge is put in a closed raw water container, whereby a large amount of hydrogen gas is generated in a short period of time and released from a whole surface of said cartridge in a form of microbubbles so as to be dissolved in raw water in the container.

7. A water reforming method comprising the steps of:
    preparing a microporous cartridge made of a sintered polypropylene material, said cartridge directly accommodating metallic magnesium particles that have been subjected to special processing comprising firing carried out at a temperature of 115° C. plus or minus 5° C. for a time period of 15 minutes plus or minus 5 minutes, black silica and titanium balls and being closed; and putting said cartridge in a closed raw water container, whereby a large amount of hydrogen gas is generated in a short period of time and released from a whole surface of said cartridge in a form of microbubbles so as to be dissolved in raw water in the container.

8. A water reformer comprising:

a microporous cartridge made of a sintered polypropylene material; and metallic magnesium particles that have been subjected to special processing comprising firing carried out at a temperature of 115° C. plus or minus 5° C. for a time period of 15 minutes plus or minus 5 minutes, black silica and titanium balls that are accommodated directly in said cartridge, said cartridge being closed after said metallic magnesium particles, black silica and titanium balls have been accommodated therein;

wherein said cartridge is put in a closed raw water container, whereby a large amount of hydrogen gas is generated in a short period of time and released from a whole surface of said cartridge in a form of microbubbles so as to be dissolved in raw water in the container.

9. A water reforming method according to claim 1, 3, 5 or 7, wherein said cartridge made of a sintered polypropylene material has micropores of about 100 to 200 microns in pore size.

10. A water reformer according to claim 2, 4, 6 or 8, wherein said cartridge made of a sintered polypropylene material has micropores of about 100 to 200 microns in pore size.

* * * * *